(12) United States Patent
Rasmussen et al.

(10) Patent No.: US 8,066,756 B2
(45) Date of Patent: Nov. 29, 2011

(54) CONTAINMENT SLEEVE AND DEPLOYMENT DEVICE

(75) Inventors: Erik E. Rasmussen, Siagelse (DK); Lars S. Nimgaard, Koege (DK)

(73) Assignee: Cook Medical Technologies LLC, Bloomington, IN (US)

( * ) Notice: Subject to any disclaimer, the term of this patent is extended or adjusted under 35 U.S.C. 154(b) by 1033 days.

(21) Appl. No.: 11/998,529

(22) Filed: Nov. 30, 2007

(65) Prior Publication Data
US 2008/0132879 A1 Jun. 5, 2008

Related U.S. Application Data

(60) Provisional application No. 60/861,860, filed on Nov. 30, 2006.

(51) Int. Cl.
*A61F 2/06* (2006.01)
(52) U.S. Cl. ...................... 623/1.12; 623/1.11; 623/1.23
(58) Field of Classification Search .................. 606/108, 606/151, 191, 194, 195, 198; 623/1.11, 1.12, 623/1.27; 600/101, 129
See application file for complete search history.

(56) References Cited

U.S. PATENT DOCUMENTS

| 5,683,451 | A  | * | 11/1997 | Lenker et al. | ................ 623/1.11 |
| 6,689,120 | B1 | * | 2/2004 | Gerdts | .......................... 604/526 |
| 7,285,130 | B2 | * | 10/2007 | Austin | ......................... 623/1.12 |

* cited by examiner

*Primary Examiner* — Tuan Nguyen
(74) *Attorney, Agent, or Firm* — Richard J. Godlewski

(57) ABSTRACT

A deployment device for deploying stents, stent-grafts and other implants into a patient includes a catheter (112) with a containment sheath (116). Held onto the catheter (112) is a stent-graft structure (120). The containment sheath (116) extends over the entirety of the stent graft section (122) so as to constrain it in its entirety on the catheter (112), until the sheath (116) is removed. The containment sheath (116) extends from the distal position (126) of the stent graft section (122) to the tip (114) and then into the central lumen (128) of the catheter (112). It may extend throughout the lumen (128) to the proximal end of the deployment device (10), in other words to the external manipulation section of the delivery device (10). The sheath (116) is withdrawn by pulling towards the external manipulation section of the delivery device. As this is effected, the containment sheath (116) is pulled over the end (114) of the catheter and into the central lumen (128) of the catheter (112). As this occurs the containment sheath (116) is in effect withdrawn into the catheter (112), thereby releasing the stent-graft section (122) gradually. Continued pulling will gradually pull the entirety of the containment sheath (116) into the open end of the catheter (112), thereby releasing the entirety of the stent-graft section (122).

18 Claims, 2 Drawing Sheets

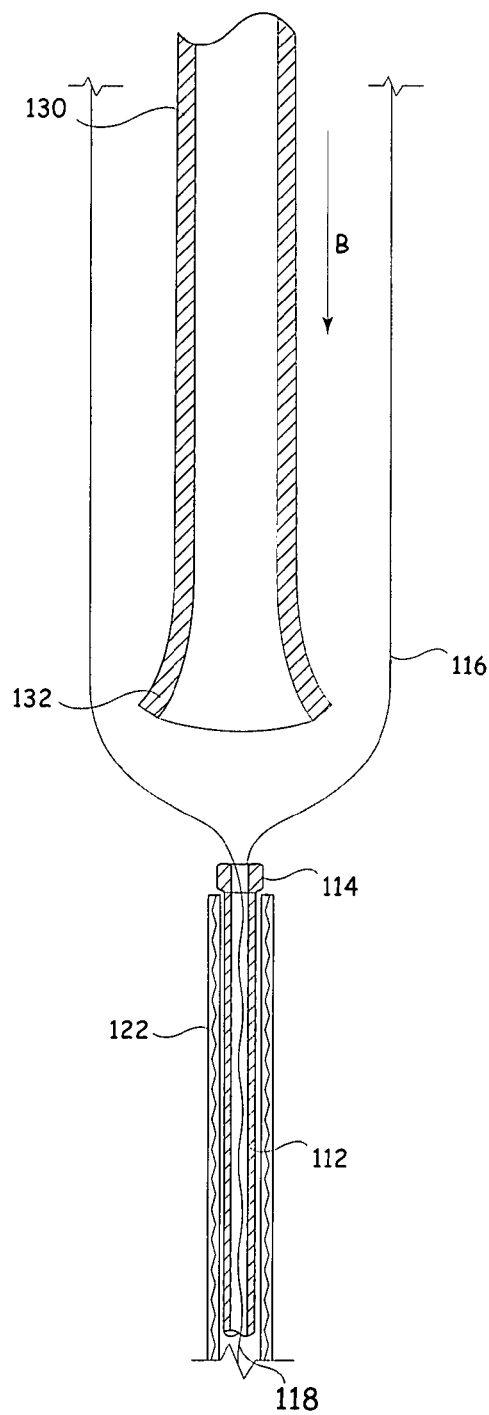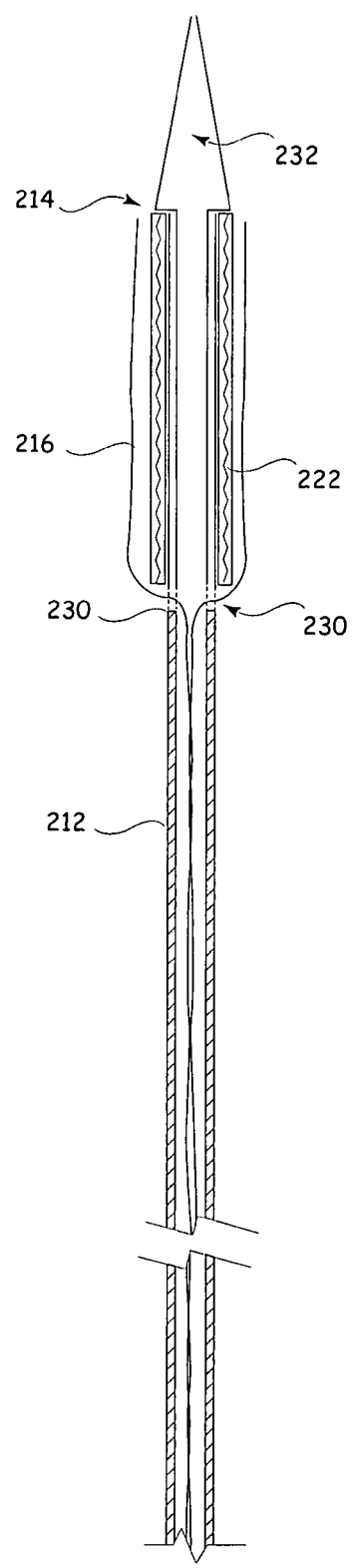
FIG. 4
FIG. 5

CONTAINMENT SLEEVE AND DEPLOYMENT DEVICE

CROSS-REFERENCE TO RELATED APPLICATIONS

This application claims priority of provisional application Ser. No. 60/861,860, filed Nov. 30, 2006.

TECHNICAL FIELD

The present invention relates to a containment sleeve and to a deployment device for deploying a stent, a stent-graft or other implant within a patient, for example by intraluminal delivery.

BACKGROUND OF THE INVENTION

The use of delivery devices employing catheters have long been known and used for a variety of medical procedures for establishing, re-establishing or maintaining passages, cavities or lumens in vessels, organs or ducts in human and veterinary patients. For these procedures, it has also long been known to deliver an implant by means of a catheter, often intraluminally. For example, a stent, stent-graft, filter or occlusion device may be delivered intraluminally from the femoral artery for deployment.

For procedures which implant into the patient a prosthesis or other device, the device to be implanted is normally held onto the catheter in a compressed state and then released from the catheter so as to expand to its normal operating state, prior to withdrawal of the catheter from the patient to leave the implant in position.

A variety of delivery mechanisms are known in the art. These generally involve positioning the implant on a distal part of the delivery device, that is at an end furthest from the external manipulation end used by the clinician during the deployment procedure. The prosthesis or implant is normally held to the distal end of the catheter by a suitable restraining mechanism, such as restraining wires or the like. It is also conventional to cover the implant with a sheath in order to protect the implant and also the patient's lumens or organs during the delivery process. Once the implant has been positioned at the location in which it is to be released, the sheath is removed to expose the implant. This is then expanded, either automatically if the implant is of the self-expanding type or by a suitable expanding mechanism if not, such as by means of an expansion balloon.

In cases where a sheath or other covering is provided, some delivery devices include a mechanism by which the sheath can be withdrawn by being pulled back towards the external manipulation end of the delivery device, that is towards the surgeon or other clinician. For this purpose, the delivery device typically includes a pusher member held within the outer sheath and to which an opposing force can be applied during the action of pulling the sheath back. Delivery apparatus of this type is well known, for example for the delivery of stents and stent-grafts, particularly to the aorta.

In other instances it is desirable to have a device which does not require retraction or withdrawal of the containment sheath prior to expansion of the implant. This may be, for example, in cases where the device and the implant have a small outer diameter, in which case the components of the delivery device are desirably as small and as thin as possible whilst maintaining their ability to provide the required delivery function.

In such instances, the containment sheath may be of a type which can be split open so as to allow expansion of the implant from its contracted state. The containment sheath, in this example could be withdrawn from the patient but is often left within the patient, trapped between the expanded implant and the internal walls of the patient's lumen or organ. In such a case, the material forming the sheath may be of a biodegradable or bioabsorbable material.

WO-98/20812 discloses a series of examples of sleeve splitting mechanisms for splitting the containment sleeve or sheath provided to protect an implant during deployment. In some of the examples described, the sleeve is provided with a plurality of weakening points which tear upon expansion of a balloon used for expanding the stent, stent-graft or other implant held on the catheter. Other examples provide for a cutting wire to cut through the sleeve and hence to release the implant held therewithin.

An arrangement using a cutting wire is also disclosed in EP-A-1,200,017, U.S. Pat. Nos. 6,576,005 and 6,183,481.

WO-99/47074 discloses another arrangement, in which in place of a sleeve there is provided a thread which is wound around the stent held on the catheter and which is then unwound so as to release the stent.

SUMMARY OF THE INVENTION

The present invention seeks to provide an improved implant delivery device and an improved containment sleeve or sheath for containing a stent, a stent-graft or other implant on a delivery device.

According to an aspect of the present invention, there is provided a delivery device for delivering an implant into a patient, including a catheter provided with a distal region for holding a device to be located within a patient; the catheter including an internal lumen therewithin; a containment sheath being provided to contain an implant at or proximate the distal end of the catheter, wherein the containment sheath is drawable through the inner lumen of the catheter during delivery of the implant.

In an embodiment, the containment sheath or at least a section thereof extends into the lumen of the catheter to an external manipulation portion of the delivery device. In another embodiment, there is provided a drawing element attached to or integral with the containment sheath and operable to draw the containment sheath through the inner passage of the catheter. Such a drawing element could, for example, be a wire or thread.

In some embodiments, the sheath is drawn through the tip of the catheter. Thus, the sheath exposes a distal end of the implant held on the catheter first and is in practice inverted into the catheter as it is removed. The distal end of the implant it the end furthest downstream, in the case of an aortic implant furthest from the heart.

In other embodiments, the sheath is drawn directly in a direction outside the patient, that is directly towards the external manipulation section of the delivery device. For this purpose, the catheter is provided with an aperture therein at an intermediate position along its length, through which the sheath is made to pass during its removal. Thus, in these embodiments, the proximal end of the implant is released first. The proximal end of the implant is the end furthest upstream, in the case of an aortic implant closest to the heart.

In both instances, the removal of the containment sheath is gradual, from one end of the implant to the other. This can provide for a gradual release of the implant from the delivery catheter, in cases where the implant is not otherwise tied to the catheter or where any restraining mechanism provided is released at the same time as removal of the sheath.

It is preferred that the implant, for example the stent or stent-graft, can self-expand upon removal of the containment sheath, although in some applications it may be desired to provide for a separate expansion device, such as a balloon or other expansion member of a type known in the art.

The advantage of this structure is that a relatively thin containment sheath can be provided. It can also allow for expansion of the implant from its distal, that is downstream, end first, that is in a sequence contrary to that provided with prior art containment sheaths which are withdrawn first from the proximal end of the implant, that is from the tip of the catheter. Such prior art systems can only provide for expansion of the distal end of the implant first by provision of other expansion mechanisms, such as release wires, balloons, bulbous expansion members and the like.

Furthermore, it is not necessary to leave any part of the containment sheath within the patient, such as is the case with a number of prior art systems which provide for splitting or cutting of the sheath.

This system is particularly advantageous for delivering devices which are of a complex structure, such as having different types of structure along their length. An example is an aortic graft device which includes a stent-graft integral with a corrugated or elephant-trunk section of the type disclosed, for example, in U.S. Pat. No. 6,773,457. With such a device, the elephant trunk section may not be compressed for delivery but rather delivered to an opened lumen of a patient, such as the aorta, to treat an aortic aneurysm. With such a device the stent-graft section of the implant is held in a compressed state before delivery to a portion of an aortic lumen which is not cut open by the surgeon. With such a device, it is obviously advantageous to expand the stent-graft from the position of the corrugated section or elephant trunk section.

Advantageously, the distal end of the catheter is provided with an end member for smooth passage of the containment sheath as it is withdrawn into the inner passage of the catheter. This end portion is preferably in the form of an enlarged head. In the preferred embodiment, the end portion is made of metal or other substantially rigid material.

The end portion is preferably rotatable relative to the catheter. This facilitates withdrawal of the sheath even if this twists during the withdrawal operation.

In some embodiments, the containment sheath may be provided with longitudinal strengthening elements therewithin to assist in its withdrawal process. The longitudinal strengthening elements may be strands or wires of reinforcement material.

Advantageously, the delivery device includes a handle or similar element at the proximal end of the delivery device for pulling the sheath or pulling member of the sheath, so as to withdraw the sheath from its position covering the implant.

The sheath can be shorter in length than the implant or can be substantially the same length as the implant.

The sheath is preferably indistensable and can be composed of a medical grade material such as nylon, polytetrafluoroethylene, PET, polyethylene or a polycaprolactam, or any other material, including compliant-materials covered with non-compliant layer of material of the type described above.

A lubricious surface can be provided on the sleeve. The lubricious surface can comprise a layer of a hydrophilic material on the sleeve or can be formed by surface modification of the sleeve.

In an embodiment, the sheath could be splittable to assist in the operation of withdrawing the sleeve through the catheter.

BRIEF DESCRIPTION OF THE DRAWING

Embodiments of the present invention are described below, by way of example only, with reference to the accompanying drawings, in which:

FIG. 4 is a schematic view in cross-section of an embodiment of sheath fitting apparatus.

FIG. 5 shows in cross-section a distal end of a catheter of an implant deployment system showing is a second embodiment of containment sheath.

DETAILED DESCRIPTION

Figure 1:
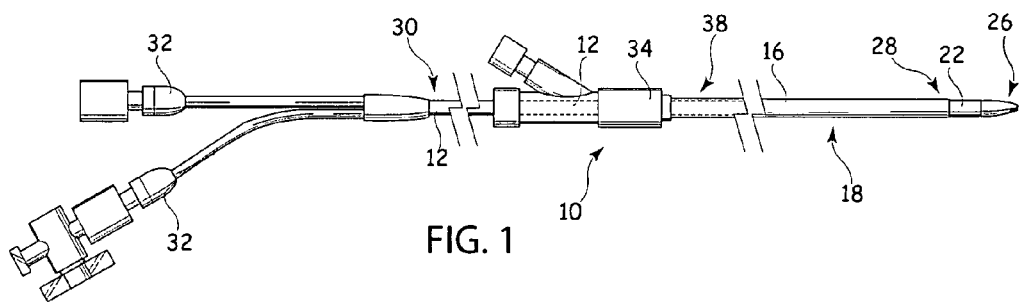
FIG. 1 is a side view of an example of a prior art stent deployment device adaptable for use with the sleeve and sleeve withdrawal mechanism taught herein.

With reference first to FIG. 1, an example of a prior art stent deployment device 10 is shown, which can be adapted to use the sheath and sheath removal structure taught herein. It comprises a catheter 12, a prosthesis or other implant (not visible in FIG. 1) positioned on the catheter 12, and a sleeve 16 carried on the catheter 12. In this case the implant is a stent.

The sleeve 16 has a portion 18 extending fully over and containing the implant at a position adjacent the tip 26 of the delivery device 10 and typically abuts a flexible tip 22 of the device 10. The stent can be self-expanding upon removal of the sleeve portion 18 or can be expanded by a separate expansion mechanism such as a balloon or bulbous member, of a type known in the art.

One or more conventional fluid couplings 32 is provided at the proximal end 30 of the catheter 12, through which a fluid can be supplied such as a medicament or compound required for the stent delivery procedure, for example a saline solution.

Although not depicted, another lumen extends longitudinally through the catheter between the distal end thereof and one of the proximal couplings 32. This lumen is typically utilized for passing the catheter over a guide wire which is first positioned in a vessel prior to insertion of the catheter 12.

As indicated, the implant can be any type of implant, prosthesis, stent or stent graft deliverable by catheter.

It is normally preferred that the sleeve 16 is substantially the same length as the catheter 12 and includes a proximal end 38 fixed to the catheter 12, for example, fixed near the proximal end 30 of the catheter 12 at the coupling 34.

The sleeve 16 can be composed of any of a variety of materials, some more suited to particular applications than others. The sleeve 16 should be composed of a medical grade material, which can be either physiologically inert or biodegradable.

Suitable inert materials for the sleeve 16 include nylon, polyethylene, a polycaprolactam or polytetrafluoroethylene (PTFE). Nylon is preferred, especially in comparison to PTFE, since the latter can be subject to recoil after being drawn over the implant. A lubricious surface can be provided on the sleeve 16 to facilitate advancement of the device 10 through the vessel or the like into which the stent is introduced. The lubricious surface can be formed by surface modification of the sleeve 16, for example, by ion beam bombardment or implantation, which is commercially available from Spire Corporation, Bedford, Mass. Alternatively, the lubricious surface can comprise a separate layer of a suitable material placed on the sleeve 16, such as a hydrophilic material. In some prior art systems the sleeve is slidable towards the proximal end of the device 10, that is towards the surgeon or other operator of the device 10. In other embodiments, the sleeve 16 may be splittable upon expansion of the stent held therewithin, for example splittable upon expansion of a balloon provided to expand the stent. In the case of a splittable sleeve 16, the sleeve 16 may be fixed to the catheter 12.

Figure 2:
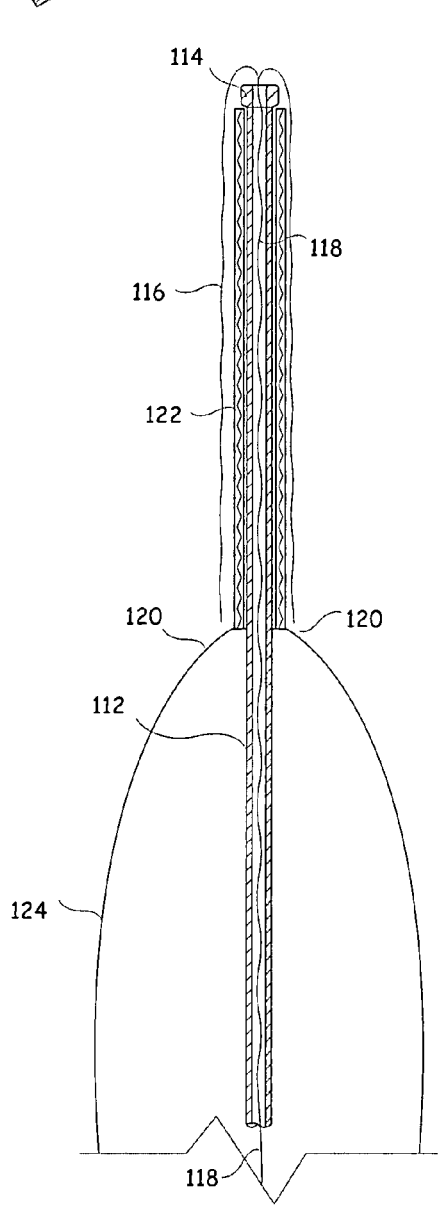
FIG. 2 shows in cross-section a distal end of a catheter of an implant deployment system showing fitted thereto a first embodiment of containment sheath.

Referring now to FIG. 2 there is shown in schematic form and in cross-section an embodiment of the distal end of a catheter 112 being provided with a preferred embodiment of constraining or containment sheath 116 thereon. In this instance, the catheter 112 is provided with an enlarged end 114, which is preferably a separate element to the catheter 112 and most preferably is rotatable relative to the catheter 112. The enlarged end 114 is advantageously made of metal. It will be apparent to the skilled person, however, that the end 114 need not be enlarged and could be made of the same material as the catheter 112, whether or not it is enlarged.

Held onto the catheter 112 is a stent-graft structure 120 which in this embodiment includes a stent graft section 122 and a corrugated section 124, otherwise known as an elephant trunk. The containment sleeve or sheath 116 extends, in this embodiment, over the entirety of the stent graft section 122 so as to constrain it in its entirety on the catheter 112, until the sheath 116 is removed. In this embodiment, the elephant trunk section 124 is not constrained by the sheath 116. This arrangement is typical for situations where the elephant trunk section 124 is fitted by open-lumen delivery methods and in which the stent-graft section 122 is inserted into a closed portion of the lumen.

The containment sheath 116, in this embodiment, extends from the distal position 126 of the stent graft section 122 to the tip 114 and then into the central lumen 128 of the catheter 112. It extends throughout the lumen 128 to the proximal end of the deployment device 10, in other words to the external manipulation section of the delivery device 10. Thus, in this embodiment, the part of the containment sheath 116 which extends through the lumen 128 is also of tubular form, simply collapsed onto itself to form a relatively small diameter pulling member for pulling the external part of the containment sheath 116 to release the stent-graft section 122, as described below in further detail.

In alternative embodiments, the containment sheath 116 is coupled to a pulling member 118. The pulling member 118 may, for example, be a thread or wire which is coupled to, preferably integral with, the containment sheath 116. It may be coupled to a part of or preferably substantially to the entirety of the length of the containment sheath 116, for example by being embedded therewith.

Not shown in the drawings but readily appreciated by a person skilled in the art, the external manipulation section of the delivery device may be provided with a handle or gripper for gripping the pulling member 118 and for assisting the surgeon or clinician in pulling the pulling member 118 so as to remove the sheath 116. Handles or grippers of this nature are well known, for example used extensively in connection with release wires and other components of the delivery system, and therefore need not be described in any further detail herein.

The sheath 116 may be made of any suitable material, for example, nylon, polyethylene, PET, a polycaprolactam or polytetrafluoroethylene (PTFE). Nylon is preferred, especially in comparison to PTFE, since the latter can be subject to recoil after being drawn over the implant.

The containment sheath 116 is preferably made of a non-compliant material and could be made of the same material as that for expansion balloons.

Figure 3:
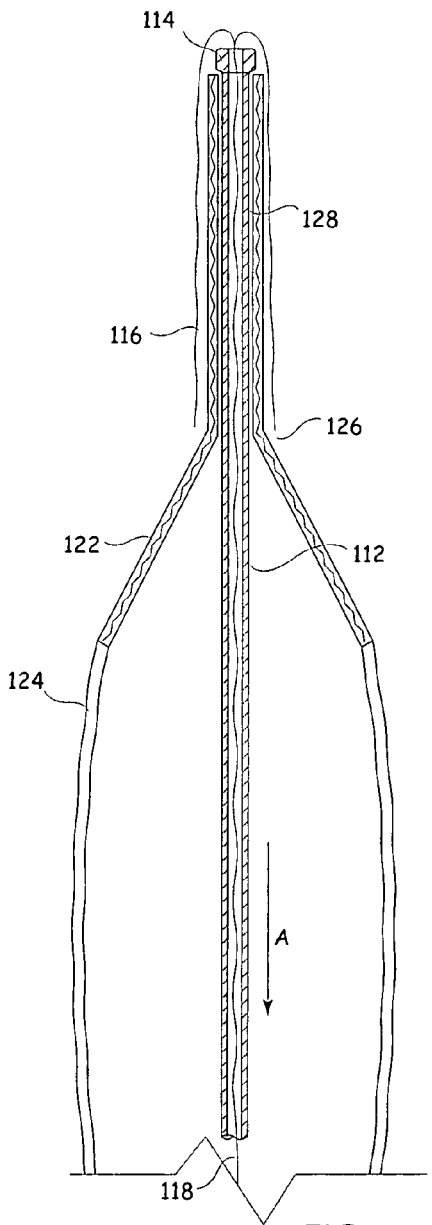
FIG. 3 is a view similar to FIG. 2 showing the sheath of FIG. 2 in a partially withdrawn condition.

Referring now to FIG. 3, the embodiment shown in FIG. 2 is illustrated with the sheath 116 having been partially withdrawn from its location over the stent graft section 122. This is achieved by pulling on the pulling member 118 in the direction of the arrow A, that is towards the external manipulation section of the delivery device. As a pulling action in direction A is effected, the containment sheath 116 is pulled over the end 114 of the catheter and into the central lumen 128 of the catheter 112. As this occurs the containment sheath 116 is in effect withdrawn into the catheter 112, thereby releasing the stent-graft section 122 gradually. This arrangement is particularly advantageous for devices of the type shown in FIGS. 2 and 3, that is for prostheses which include one portion which is not compressed onto the delivery catheter or any other prosthesis which benefits from being expanded from its distal end first, that is from its downstream end first.

In some embodiments the containment sheath 116 need not extend over the entirety of the stent graft section 122 but may only extend over a part of this. In other words, the assembly could be provided in a form similar to that shown in FIG. 3, rather than the configuration shown in FIG. 2.

Continued pulling on the pulling member 118 in the direction of arrow A will pull gradually the entirety of the containment sheath 116 into the open end of the catheter 112, thereby releasing the entirety of the stent graft section 122. As soon as the entirety of the containment sheath 116 is removed from the stent graft section 122, the catheter 112 can be easily removed from the patient by simply withdrawing this, leaving the prosthesis in position. The procedure is extremely simple, requiring no further manipulation of components of the delivery device in order to remove it from the patient.

During the procedure of pulling the containment sheath 116 into the central lumen 128 of the catheter 112, it is possible to effect or experience some twisting moment, caused for example by the clinician's wish to control the final orientation of the device 120. A twisting moment could also be caused by twisting of the pulling member 118 and possibly also, generally to a smaller extent, by twisting of the containment sheath 116 as it is fitted over the stent-graft section 122 during the assembly procedure, for example as a result of manufacturing tolerances. For this reason, it is preferred that the end member 114 is rotatable as this will adjust to remove or reduce any twisting torque, thereby facilitating the procedure of withdrawing the containment sheath 116.

The structure shown in FIGS. 2 and 3 is not necessarily limited to deployment of prosthesis of the type shown in these Figures. The structure could equally be used to deliver any stent, stent-graft or other implant or prosthesis to a patient which can be deployed from a distal end of the implant prosthesis, that is from its end furthest from the tip 114 of the catheter section 112. Similarly, as explained above, any stent, stent-graft or other implant or prosthesis held in this manner need not be covered entirely by containment sheath 116 but may be only partially covered thereby. This can sometimes facilitate the accurate placement of the implanted prosthesis by virtue of it already being partially expanded.

Referring now to FIG. 4, there is shown an embodiment of mechanism for fitting the containment sheath 116 over the implant to be held thereby, in this case the stent graft section 122. In this embodiment, there is provided a reversing element 130 in the form of a substantially cylindrical member with flared opening 132. This fits within the containment sheath 116, which at this stage extends in the same direction as the catheter 112. The sheath 116 is everted by moving the member 130 towards the end of the catheter 112 and then over the catheter. Typically, this movement is achieved by moving the member in the direction of arrow B, although of course, the member 130 could be fixed with the catheter 112 being pushed into the tubular everting member 130. The flared end 132 assists in the eversion process.

The skilled person will appreciate that there are known in the art other mechanisms which could be suitable for fitting the containment sheath 116 onto the end of the catheter and stent graft section 122.

In this regard, it will be appreciated by a person skilled in the art that for this eversion mechanism, the containment sheath 116 is preferably slightly conformable, that is slightly stretchable, so as to assist in the assembly process, while still remaining sufficiently tight to provide sufficient radial force to retain the implant or prosthesis held thereby in its constrained position until the containment sheath 116 is removed therefrom.

FIG. 4 shows the stent graft 122 already compressed on the catheter 112. In some instances, the compression of the stent graft 122 can be effected in the same process as eversion of the sheath 116, by any of the known methods. As these are known and practiced in the art, they are not described herein.

In some embodiments, the containment sheath 116 could be of a nature in which it could be shrunk onto the implant following its eversion, by its inherent resiliency or by heat-shrinkage or other suitable method.

The above described embodiment provides for the implant to be released starting from its distal end. Referring now to FIG. 5, in an alternative, the sheath could be slidable directly towards the exterior of the deployment device, in which case the sheath 216 would not pass through the open end 214 of the sheath 216 at nose cone 232. Instead, it is envisaged that the catheter 212 would be provided with at least an opening 230 at some intermediate position along its length, preferably but not necessarily, proximate the distal end of the implant 222. In this case, the sheath would be pulled so as to be removed first from the proximal end of the implant 222, that is from its end closest to the tip 214 of the catheter. For this purpose, the sheath 216 may split longitudinally as it is pulled into the opening in the catheter, so as to unwrap itself from the catheter at the same time.

The person skilled in the art will appreciate that this structure of constraining or retaining sheath is very simple, requires few mechanical components and thereby provides a device which is simple and which can be minimized, in some cases substantially more than existing devices which require a number of additional components in order to carry out the implant deployment procedure.

It also provides a mechanism by which an implant can be deployed from its downstream end first, therefore in a different manner compared to systems which only provide for deployment from an upstream or proximal end of the implant first. Furthermore, the surgeon or clinician, during the deployment procedure, is directly controlling the removal of the sheath rather than effecting an action which itself causes or leads to removal of a containment sheath, such as is the case when a surgeon is activating a sheath tearing mechanism or other mechanism which only by what in effect is a chain event would then activate removal, tearing or cutting of the sheath.

What is claimed is:

1. A delivery device for delivering a stent or a stent-graft into a patient, including a catheter provided with a distal region for holding thereon a stent or a stent-graft on the distal region; the catheter including an internal lumen therewithin and a distal end; a containment sheath being provided with a distal portion and a proximal portion, wherein the distal portion of the containment sheath is everted over the distal region of the catheter to contain the stent or the stent-graft, wherein the proximal portion of the containment sheath located in the internal lumen, and wherein the distal portion of the containment sheath is pulled over the distal end and through the internal lumen of the catheter during delivery of the stent or the stent-graft.

2. A delivery device according to claim 1, wherein at least the proximal portion of the containment sheath extends into the internal lumen of the catheter to an external manipulation portion of the delivery device.

3. A delivery device according to claim 1, including a pulling element attached to or integral with the containment sheath and operable to pull the containment sheath through the internal lumen of the catheter.

4. A delivery device according to claim 3, wherein the pulling element is a wire or thread.

5. A delivery device according to claim 1, wherein the sheath is pulled directly towards an external manipulation section of the delivery device.

6. A delivery device according to claim 1, wherein the containment sheath is made from a non-compliant material.

7. A delivery device according to claim 6, wherein the sheath is made from: nylon, PTFE, PET, polyethylene or a polycaprolactam or any combination thereof.

8. A delivery device according to claim 1, wherein the distal end of the catheter is provided with an end member for smooth passage of the containment sheath as it is withdrawn into the inner passage of the catheter.

9. A delivery device according to claim 8, wherein the end member is in the form of an enlarged head.

10. A delivery device according to claim 8, wherein the end member is made of metal or other substantially rigid material.

11. A delivery device according to claim 8, wherein the end member is rotatable relative to the catheter.

12. A delivery device according to claim 1, wherein the containment sheath is provided with longitudinal strengthening elements therewithin.

13. A delivery device according to claim 12, wherein the longitudinal strengthening elements are strands or wires of enforcement material.

14. A delivery device according to claim 1, including a handle at the proximal end of the delivery device coupled to at least one of the sheath or a pulling member attached to the sheath.

15. A delivery device according to claim 9, wherein the end member is made of metal or other substantially rigid material.

16. A delivery device according to claim 9, wherein the end member is rotatable relative to the catheter.

17. A delivery device according to claim 10, wherein the end member is rotatable relative to the catheter.

18. A delivery device according to claim 8, including a handle at an proximal end of the delivery device coupled to at least one of the sheath or a pulling member attached to the sheath.

* * * * *